US012758125B2

(12) United States Patent
Sun et al.

(10) Patent No.: US 12,758,125 B2
(45) Date of Patent: Oct. 13, 2026

(54) MICRO-PILLAR WORKING ELECTRODES DESIGN TO REDUCE BACKFLOW OF HYDROGEN PEROXIDE IN GLUCOSE SENSOR

(71) Applicant: Medtronic MiniMed, Inc., Northridge, CA (US)

(72) Inventors: Zhenzhong Sun, Northridge, CA (US); Xin Heng, Glendale, CA (US); Rui Kong, Porter Ranch, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 17/979,204

(22) Filed: Nov. 2, 2022

(65) Prior Publication Data

US 2023/0055521 A1 Feb. 23, 2023

Related U.S. Application Data

(63) Continuation of application No. 16/528,813, filed on Aug. 1, 2019, now Pat. No. 11,523,757.

(51) Int. Cl.
*A61B 5/145* (2006.01)
*A61B 5/1486* (2006.01)

(52) U.S. Cl.
CPC ........ *A61B 5/14532* (2013.01); *A61B 5/1486* (2013.01); *A61B 5/14546* (2013.01); *A61B 2562/046* (2013.01); *A61B 2562/125* (2013.01)

(58) Field of Classification Search
CPC .............. A61B 5/14532; A61B 5/1486; A61B 5/14546; A61B 2562/046; A61B 2562/125
See application file for complete search history.

(56) References Cited

U.S. PATENT DOCUMENTS

| | | | |
|---|---|---|---|
| 4,755,173 | A | 7/1988 | Konopka et al. |
| 5,391,250 | A | 2/1995 | Cheney, II et al. |
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |

(Continued)

FOREIGN PATENT DOCUMENTS

| | | |
|---|---|---|
| CN | 102556952 | 1/2015 |
| CN | 107205647 A | 9/2017 |

(Continued)

OTHER PUBLICATIONS

PCT International Search Report & Written Opinion dated Aug. 22, 2018, International Application No. PCT/US18/22805.

(Continued)

*Primary Examiner* — Jason M Sims
*Assistant Examiner* — Kyle W. Kretzer
(74) *Attorney, Agent, or Firm* — GATES & COOPER LLP

(57) ABSTRACT

An electrochemical sensor including a working electrode having an arrangement of pillars defining channels between the pillars. The channels increase confinement of a byproduct produced in an electrochemical reaction used during sensing of an analyte, so as to increase interaction of the byproduct with the working electrode. A number of working embodiments of the invention are shown to be useful in amperometric glucose sensors worn by diabetic individuals.

21 Claims, 10 Drawing Sheets

(56) References Cited

U.S. PATENT DOCUMENTS

| | | | |
|---|---|---|---|
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Stoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 10,213,144 | B2 | 2/2019 | Kinser et al. |
| 11,523,757 | B2 * | 12/2022 | Sun .................... A61B 5/14532 |
| 2005/0260453 | A1 | 11/2005 | Jiao et al. |
| 2006/0020192 | A1 * | 1/2006 | Brister ................. A61B 5/1495 600/345 |
| 2007/0123819 | A1 | 5/2007 | Mernoe et al. |
| 2008/0214916 | A1 * | 9/2008 | Yodfat ............... A61B 5/14532 600/347 |
| 2010/0066346 | A1 | 3/2010 | Zhang et al. |
| 2010/0160861 | A1 | 6/2010 | Causey, III et al. |
| 2011/0042237 | A1 * | 2/2011 | Fukuda .................. G01N 27/27 204/400 |
| 2012/0190950 | A1 * | 7/2012 | Yang ...................... C12Q 1/001 252/514 |
| 2013/0066182 | A1 | 3/2013 | Seymour |
| 2014/0167257 | A1 * | 6/2014 | Mujeeb-U-Rahman ..................... H10D 64/20 257/737 |
| 2014/0228660 | A1 | 8/2014 | Mujeeb-U-Rahman et al. |
| 2018/0338681 | A1 | 11/2018 | Scherer et al. |
| 2019/0008425 | A1 | 1/2019 | Srinivasan et al. |
| 2019/0307378 | A1 * | 10/2019 | Adalian ............... A61B 5/1473 |
| 2023/0055521 | A1 | 2/2023 | Sun et al. |

FOREIGN PATENT DOCUMENTS

| | | | |
|---|---|---|---|
| WO | 2012100133 | A2 | 7/2012 |
| WO | 2013168956 | | 11/2013 |

OTHER PUBLICATIONS

European Examination Report dated Feb. 8, 2023 for European Patent Application No. 20761927.1.

Final Office Action dated Aug. 27, 2021 for U.S. Appl. No. 16/528,813.

Non-Final Office Action dated Jan. 20, 2022 for U.S. Appl. No. 16/528,813.

Non-Final Office Action dated Mar. 3, 2021 for U.S. Appl. No. 16/528,813.

Notice of Allowance dated Aug. 2, 2022 for U.S. Appl. No. 16/528,813.

PCT International Search Report & Written Opinion dated Oct. 2, 2020 for PCT Application No. PCT/US2020/043971.

Chinese First Examination Opinion Notice dated Jul. 12, 2024 for Chinese Application No. 202080051384.3.

Chinese Office Action dated Dec. 31, 2024 for Chinese Application No. 202080051384.3.

* cited by examiner

MICRO-PILLAR WORKING ELECTRODES DESIGN TO REDUCE BACKFLOW OF HYDROGEN PEROXIDE IN GLUCOSE SENSOR

CROSS REFERENCE TO RELATED APPLICATIONS

This application is a continuation application which claims the benefit under 35 U.S.C. § 120 of U.S. patent application Ser. No. 16/528,813, filed Aug. 1, 2019, the contents of which are incorporated herein by reference.

TECHNICAL FIELD

The invention relates to electrode compositions useful in devices such as glucose sensors used in the management of diabetes.

BACKGROUND OF THE INVENTION

Sensors are used to monitor a wide variety of compounds in various environments, including in vivo analytes. The quantitative determination of analytes in humans is of great importance in the diagnoses and maintenance of a number of pathological conditions. Illustrative analytes that are commonly monitored in a large number of individuals include glucose, lactate, cholesterol, and bilirubin. The determination of glucose concentrations in body fluids is of particular importance to diabetic individuals, individuals who must frequently check glucose levels in their body fluids to regulate the glucose intake in their diets. The results of such tests can be crucial in determining what, if any, insulin and/or other medication need to be administered.

Analyte sensors typically include components that convert interactions with analytes into detectable signals that can be correlated with the concentrations of the analyte. For example, some glucose sensors use amperometric means to monitor glucose in vivo. Such amperometric glucose sensors typically incorporate electrodes coated with glucose oxidase, an enzyme that catalyzes the reaction between glucose and oxygen to yield gluconic acid and hydrogen peroxide ($H_2O_2$). The $H_2O_2$ formed in this reaction alters an electrode current to form a detectable and measurable signal. Based on the signal, the concentration of glucose in the individual can then be measured.

However, there is a need in the art for electrochemical sensors having architectures and materials selected to improve sensor function (e.g., increase sensor stability and lifetime). Embodiments of the invention disclosed herein meet these as well as other needs.

SUMMARY OF THE INVENTION

Embodiments of the invention disclosed herein provide layered electrochemical glucose sensor designs that include sensor materials, elements and architectures that facilitate sensor functions such as sensor lifetime and stability. As noted above, during a glucose electrochemical sensing mechanism, $H_2O_2$ molecules are generated and diffuse to the working electrode of the sensor to generate the electrical signal. In conventional sensors, however, the $H_2O_2$ also diffuses to the human body by backflow, introducing an anti-body reaction believed to undesirably reduce sensor lifetime in the human body.

As discussed in detail below, we have designed a number of sensor elements, materials and architectures that improve sensor stability and lifetime and mitigate for the backflow problem. For example, embodiments of the invention include sensors designed to include an arrangement of pillars on elements such as the working electrode, wherein the pillars create channels or pathways to extend diffusion directions of the $H_2O_2$ that reduce backflow of the $H_2O_2$ to the human body and thereby increase sensor lifetime. Embodiments of the invention include an arrangement of pillars that also distributes oxygen so that the sensor response is proportional to glucose concentration rather than oxygen concentration, thereby increasing stability of the sensor.

The invention disclosed herein has a number of embodiments. Embodiments of the invention include, for example, an electrochemical analyte sensor comprising a base layer, a working electrode including an arrangement of pillars organized so as to define channels between the pillars; and a multilayer analyte sensor stack operably coupled to the arrangement of pillars. In such embodiments, the multilayer analyte sensor stack includes an analyte sensing layer including an enzyme having a composition that reacts with an analyte to form a byproduct (e.g., $H_2O_2$), the byproduct detectably altering an electrical current at the working electrode. The multilayer analyte sensor stack further includes an analyte modulating layer disposed over the analyte sensing layer, wherein the analyte modulating layer facilitates the diffusion of the analyte from an external environment to the analyte sensing layer. In various examples, the pillars can be arranged or organized to form the channels that increase confinement of the byproduct in the channels, thereby increasing interaction of the byproduct with the working electrode. In other examples, the pillars form or define the channels or conduits increasing or extending diffusion or transport of the byproduct in additional directions, thereby reducing diffusion of the byproduct to the analyte modulation layer and guiding transport of the byproduct to the conductive layer of the working electrode, e.g., to sidewalls of the pillars.

Embodiments of the invention include electrochemical analyte sensors having constellations of materials and elements that reduce diffusion or transport of the analyte to the analyte modulation layer. In certain embodiments, the analyte sensing layer is at least partially disposed in the channels in spaces between the pillars and the analyte modulation layer is disposed directly on top of the pillars. In one or more examples, the pillars have a diameter in a range of 0.01-1000 micrometers, a height in a range of 0.01-1000 micrometers, and a spacing in a range of 0.01-1000 micrometers. In other examples, the pillars have a diameter in a range of 10-15 micrometers, a height in a range of 10-15 micrometers, and a spacing in a range of 10-15 micrometers. In yet further examples, the pillars have a diameter in a range of 5-25 micrometers, a height in a range of 5-25 micrometers, and a spacing in a range of 10-25 micrometers. In yet further examples, the pillars have a diameter in a range of 0.001-1 micrometer, a height in a range of 0.001-1 micrometer, and a spacing in a range of 0.001 micrometers. Furthermore, the pillars can be organized in a variety of configurations or patterns. For example, the pillars can be arranged in a hexagonal pattern or in a serpentine pattern.

In typical embodiments, the analyte comprises glucose, the enzyme comprises glucose oxidase, and the byproduct comprises hydrogen peroxide. In one or more glucose sensing embodiments, the analyte modulation layer facilitates the diffusion of the oxygen from an external environment to the analyte sensing layer, and the arrangement of the pillars distributes the oxygen throughout the working electrode.

In a more general embodiment, a sensor electrode, comprises a base substrate; an electrode including an arrangement of pillars disposed on the base substrate, wherein the pillars form an electroactive surface of the electrode, and an analyte sensing layer coupled to the electrode, the analyte sensing layer having a composition that reacts with an analyte to form a byproduct, the byproduct detectably altering an electrical current at the electrode. The arrangement of the pillars defines one or more channels between the pillars, the one or more channels increasing confinement of the byproduct in the channels so as to increase interaction of the byproduct with the electroactive surface during sensing of the analyte.

Other embodiments of the invention include methods of making an electrochemical analyte sensor disclosed herein. Typically, such methods comprise providing a base layer; forming an arrangement of pillars defining one or more channels over a base layer, wherein the arrangement of pillars includes a conductive layer including a working electrode; forming an analyte sensing layer operably coupled to the arrangement of the pillars, the analyte sensing layer including an enzyme having a composition that reacts with an analyte to form a byproduct, the byproduct detectably altering an electrical current at the working electrode; forming an analyte modulating layer over the analyte sensing layer, wherein the analyte modulating layer facilitates the diffusion of the analyte from an external environment to the analyte sensing layer; and so that the electrochemical analyte sensor is made. The one or more channels increase confinement of the byproduct in the one or more channels such that interaction of the byproduct with the working electrode is increased. The pillars can comprise a variety of materials, including but not limited to, a metal composition comprising at least one metal selected from platinum, gold, silver, copper, titanium, chromium, and iridium.

Other embodiments of the invention include methods of sensing an analyte within the body of a mammal. Typically, these methods comprise implanting an electrochemical analyte sensor as disclosed herein in to the mammal; sensing an alteration in current at the working electrode in the presence of the analyte; and then correlating the alteration in current with the presence of the analyte, so that the analyte is sensed.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 1C and FIG. 1D are top views of the sensor embodiments illustrating the pillars can be organized in a variety of configurations or patterns, wherein FIG. 1C illustrates the pillars disposed in a hexagonal pattern and FIG. 1D illustrates the pillars disposed in a serpentine pattern.

As shown in FIG. 4, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

DETAILED DESCRIPTION OF THE INVENTION

Figure 1B:
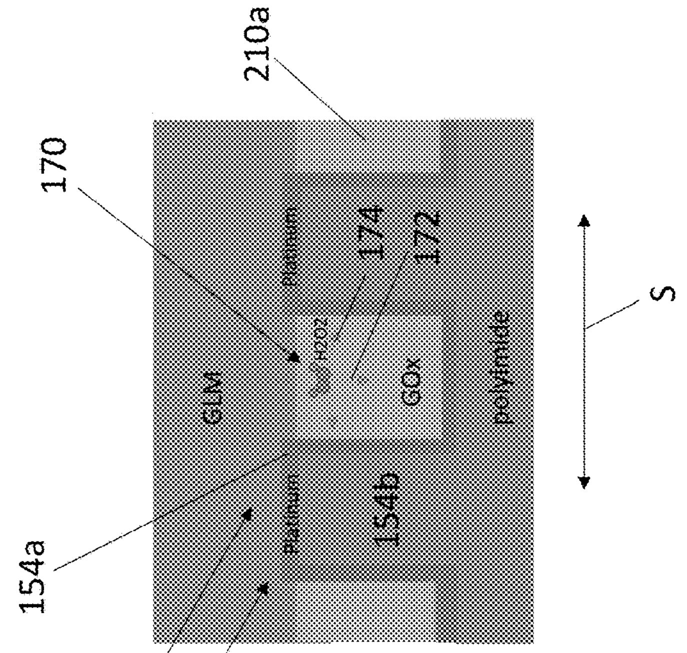
FIG. 1B is a close up view of FIG. 1A.

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All numbers recited in the specification and associated claims that refer to values that can be numerically characterized with a value other than a whole number (e.g. a thickness) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors elements, including for example, those disclosed in U.S. Patent Application Nos. 20050115832, 20050008671, 20070227907, 20400025238, 20110319734, 20110152654 and Ser. No. 13/707,400 filed Dec. 6, 2012, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042, 625, and WO 03/074107, and European Patent Application EP 1153571, the contents of each of which are incorporated herein by reference.

Illustrative Embodiments of the Invention and Associated Characteristics

Embodiments of the invention disclosed herein provide sensors designed to include multilayer analyte sensor stacks formed from selected materials and associated elements that provide the sensors with enhanced functional and/or material properties. The disclosure further provides methods for making and using such sensors. As discussed in detail below, typical embodiments of the invention relate to the use of a sensor that measures a concentration of an aqueous analyte of interest (e.g. glucose) or a substance indicative of the concentration or presence of the analyte in vivo. In some embodiments, the sensor is a subcutaneous, intramuscular, intraperitoneal, intravascular or transdermal device. Typically, the sensor can be used for continuous analyte monitoring. The sensor embodiments disclosed herein can use any known method, including invasive, minimally invasive, and non-invasive sensing techniques, to provide an output signal indicative of the concentration of the analyte of interest.

In typical embodiments of the invention, the components of the multilayer analyte sensor elements are formed from selected layers/materials and/or operably coupled to additional elements and/or disposed within the stack architecture in a specific orientation that is designed to provide these sensors with improved distribution of $H_2O_2$ and oxygen to the working electrode. The disclosure further provides methods for making and using such sensors. As discussed in detail below, typical embodiments of the invention relate to the use of a sensor that measures a concentration of an aqueous analyte of interest or a substance indicative of the concentration or presence of the analyte in vivo (e.g. glucose sensors used in the management of diabetes).

Figure 1A:
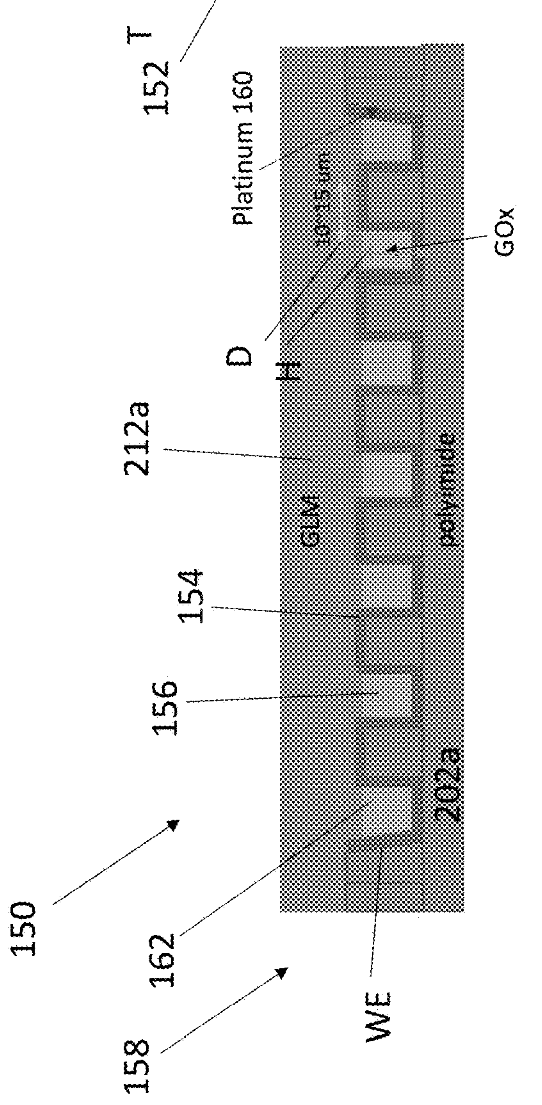
FIG. 1A illustrates a cross-sectional view of an electrochemical analyte sensor including a micro-pillar/trench working electrode, according to one or more embodiments of the present invention.

The invention disclosed herein has a number of embodiments. FIG. 1A and FIG. 1B illustrate an embodiment of the invention including, for example, an electrochemical analyte sensor 150 comprising a base layer 202*a* (e.g. a polyimide support, optionally as part of a flex-circuit assembly), a working electrode WE including an arrangement 152 of pillars 154 defining channels 156 between the pillars; and a multilayer analyte sensor 158 stack operably coupled to the arrangement of pillars. The multilayer analyte sensor stack includes:

(a) an analyte sensing layer 210*a* including an enzyme (e.g., $GO_x$) having a composition that reacts with an analyte to form a byproduct (e.g., $H_2O_2$), the byproduct 170 detectably altering an electrical current at the working electrode; and (b) an analyte modulating layer 212*a* (e.g., GLM) disposed over the analyte sensing layer, wherein the analyte modulating layer facilitates the diffusion of the analyte from an external environment to the analyte sensing layer.

FIG. 1A illustrates the pillars 154 can comprise a variety of materials, including but not limited to, a metal composition 160 comprising at least one metal selected from platinum, gold, silver, copper, titanium, chromium, and iridium. In one or more examples, the working electrode WE includes the pillars 154 each having a conductive layer 154*a* comprising the metal composition.

Embodiments of the invention include electrochemical analyte sensors having constellations of materials and elements that reduce diffusion or transport of the byproduct (e.g., $H_2O_2$) to the analyte modulation layer. FIG. 1A and FIG. 1B illustrate an example wherein analyte sensing layer 210*a* is at least partially disposed in the channels in spaces 162 between the pillars and the analyte modulation layer is disposed directly on top of the pillars. Without being bound by scientific theory, the data presented herein (FIG. 5A and FIG. 5B) provides evidence that the arrangement of pillars 154 is organized to define the one or more channels 156 or conduits that increase confinement of the byproduct in the channels 156 so as to increase interaction of the byproduct with the working electrode, or wherein the channels or conduits extend diffusion/transport directions 172 of the byproduct ($H_2O_2$) so as to reduce diffusion of the byproduct to the analyte modulation layer 210*a* and increase transport, conduit, or diffusion 174 of the byproduct to the conductive layer 154*a* of the working electrode WE.

In one or more examples, the pillars have a diameter D or width in a range of 0.001-1000 micrometers, a height H in a range of 0.001-1000 micrometers, and a spacing S in a range of 0.001-1000 micrometers. In the example illustrated in FIG. 1A, the pillars have a width of diameter D in a range of 10-15 micrometers, a height H in a range of 10-15 micrometers, and a spacing S in a range of 10-15 micrometers. In yet further examples, the pillars have a diameter or width in a range of 5-25 micrometers, a height in a range of 5-25 micrometers, and a spacing in a range of 10-25 micrometers.

Figures 1C, 1D:
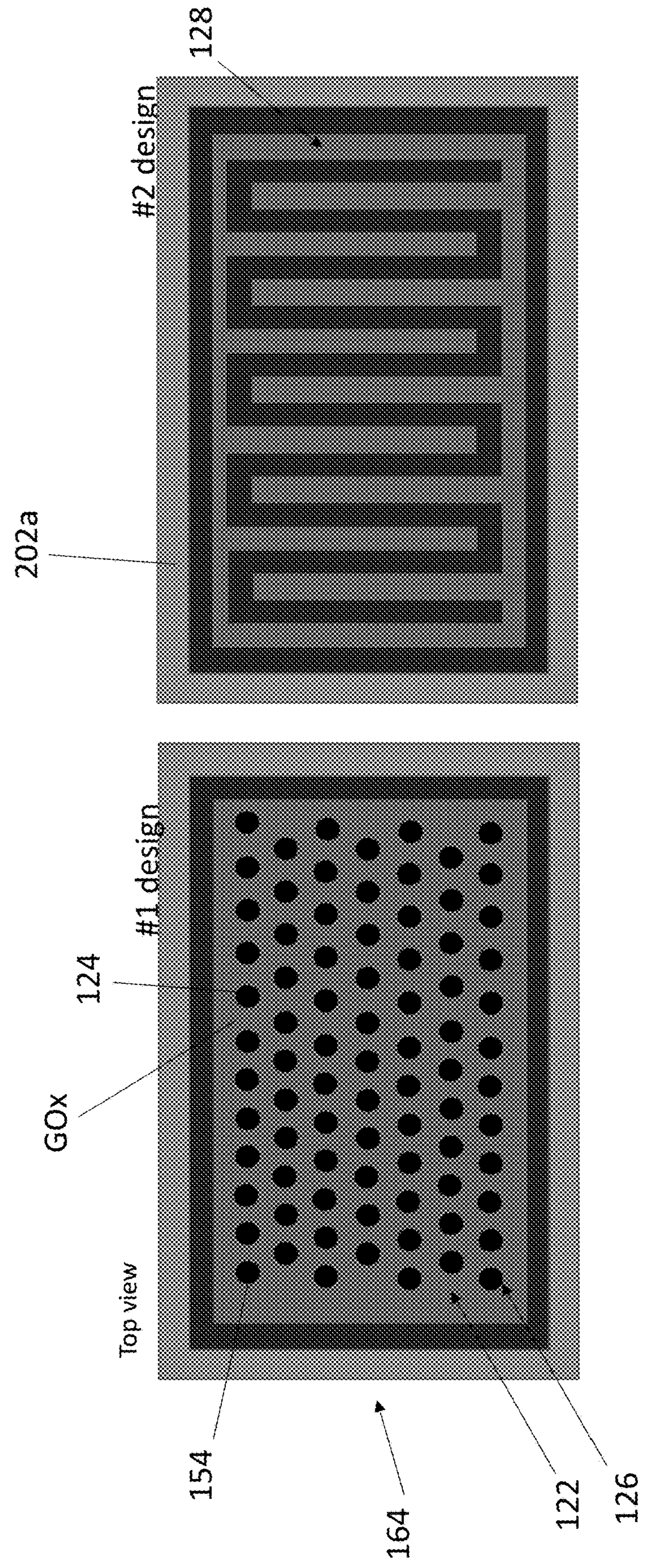

FIG. 1C and FIG. 1D illustrate the pillars 154 can be organized in a variety of configurations or patterns. FIG. 1A illustrates an example design wherein the pillars 154 are arranged in a hexagonal pattern 164 or to form a pattern including a repeating triangular unit 122 wherein pillars are positioned at apexes 124 of a triangle 126. Other examples include the pillars disposed so as to form a pattern including a repeating rectangular or square unit wherein the pillars are positioned at corners of a square or rectangle. FIG. 1D illustrates an example design wherein the pillars 154 are arranged in a serpentine pattern 128. The pattern of pillars can be selected to control confinement of the byproduct and/or extend diffusion pathways for the byproduct, thereby reducing transport/diffusion of the byproduct towards the analyte modulation layer and increasing interaction of the byproduct with the working electrode.

In typical embodiments, the analyte comprises glucose, the enzyme comprises glucose oxidase, and the byproduct comprises hydrogen peroxide. Without being bound by scientific theory, the data herein (FIGS. 6A-6D) provides evidence that the analyte modulation layer in a glucose sensor embodiment facilitates the diffusion of the oxygen from an external environment to the analyte sensing layer, and the arrangement of pillars distributes the oxygen throughout the working electrode.

Other embodiments of the invention include methods of making an electrochemical analyte sensor disclosed herein. Typically, such methods comprise providing a base layer; forming an arrangement of pillars defining one or more channels over a base layer, wherein the arrangement of pillars includes a conductive layer having a working electrode; forming an analyte sensing layer operably coupled to the arrangement of the pillars, the analyte sensing layer including an enzyme having a composition that reacts with an analyte to form a byproduct, the byproduct detectably altering an electrical current at the working electrode; forming an analyte modulating layer over the analyte sensing layer, wherein the analyte modulating layer facilitates the diffusion of the analyte from an external environment to the analyte sensing layer; and so that the electrochemical analyte sensor is made.

The arrangement of the pillars can be formed using sputtering or physical vapor deposition techniques and electroplating, for example. Examples of methods for depositing pillars in a sensor working electrode of an electrochemical sensor are described in US. Patent Publication No. 2019-0008425 A1 entitled "METAL PILLAR DEVICE STRUCTURES AND METHODS FOR MAKING AND USING THEM IN ELECTROCHEMICAL AND/OR ELECTROCATALYTIC APPLICATIONS." In one or more examples, the arrangement of pillars are formed by patterning pillars on or in the base layer 202*a* and depositing a conductive layer 154*a* comprising the metal composition 160 (e.g., using sputtering or physical vapor deposition) on the pillars formed in the base layer so that the conductive layer contours the pillars. In one or more examples, the forming the pattern of pillars in the base layer comprises depositing a mask having the desired pattern on the base layer, and etching the base layer through the mask to transfer the pattern of pillars into the base layer. In one or more examples, the pillars are defined in the base layer using photolithography. In one or more examples, the mask has the pattern designed to form the arrangement of pillars for controlling the diffusion or transport of the byproduct as described herein (e.g., such that the one or more channels increase confinement of the byproduct in the one or more channels and interaction of the byproduct with the working electrode is increased).

Other embodiments of the invention include methods of sensing an analyte within the body of a mammal. Typically these methods comprise implanting an electrochemical analyte sensor as disclosed herein in to the mammal; sensing an alteration in current at the working electrode in the presence of the analyte; and then correlating the alteration in current with the presence of the analyte, so that the analyte is sensed.

In typical embodiments of the invention, electrochemical sensors are operatively coupled to a sensor input capable of receiving signals from the electrochemical sensor; and a processor coupled to the sensor input, wherein the processor is capable of characterizing one or more signals received from the electrochemical sensor. In certain embodiments of the invention, the electrical conduit of the electrode is coupled to a potentiostat (see, e.g. FIG. 4). Optionally, a pulsed voltage is used to obtain a signal from an electrode. In typical embodiments of the invention, the processor is capable of comparing a first signal received from a working electrode in response to a first working potential with a second signal received from a working electrode in response to a second working potential. Optionally, the electrode is coupled to a processor adapted to convert data obtained from observing fluctuations in electrical current from a first format into a second format. Such embodiments include, for example, processors designed to convert a sensor current Input Signal (e.g. ISIG measured in nA) to a blood glucose concentration.

In many embodiments of the invention, the sensors comprise a biocompatible region adapted to be implanted in vivo. In some embodiments, the sensor comprises a discreet probe that pierces an in vivo environment. In embodiments of the invention, the biocompatible region can comprise a polymer that contacts an in vivo tissue. Optionally, the polymer is a hydrophilic polymer (e.g. one that absorbs water). In this way, sensors used in the systems of the invention can be used to sense a wide variety of analytes in different aqueous environments. In some embodiments of the invention, the electrode is coupled to a piercing member (e.g. a needle) adapted to be implanted in vivo. While sensor embodiments of the invention can comprise one or two piercing members, optionally such sensor apparatuses can include 3 or 4 or 5 or more piercing members that are coupled to and extend from a base element and are operatively coupled to 3 or 4 or 5 or more electrochemical sensors (e.g. microneedle arrays, embodiments of which are disclosed for example in U.S. Pat. Nos. 7,291,497 and 7,027,478, and U.S. patent Application No. 20080015494, the contents of which are incorporated by reference).

In some embodiments of the invention, the apparatus comprises one or more working electrodes, counter electrodes and reference electrodes, optionally clustered together in units consisting essentially of one working electrode, one counter electrode and one reference electrode; and the clustered units are longitudinally distributed on the base layer in a repeating pattern of units. In some sensor embodiments, the distributed electrodes are organized/disposed within a flex-circuit assembly (i.e. a circuitry assembly that utilizes flexible rather than rigid materials). Such flex-circuit assembly embodiments provide an interconnected assembly of elements (e.g. electrodes, electrical conduits, contact pads and the like) configured to facilitate wearer comfort (for example by reducing pad stiffness and wearer discomfort).

As noted above, the sensor electrodes of the invention are coated with a plurality of materials having properties that, for example, facilitate analyte sensing. In typical embodiments of the invention, an analyte sensing layer is disposed directly on a working electrode, and includes an agent that is selected for its ability to detectably alter the electrical current at the working electrode in the presence of an analyte. In the working embodiments of the invention that are disclosed herein, the agent is glucose oxidase, a protein that undergoes a chemical reaction in the presence of glucose that results in an alteration in the electrical current at the working electrode. These working embodiments further include an analyte modulating layer disposed over the analyte sensing layer, wherein the analyte modulating layer modulates the diffusion of glucose as it migrates from an in vivo environment to the analyte sensing layer. In certain embodiments of the invention, the analyte modulating layer comprises a hydrophilic comb-copolymer having a central chain and a plurality of side chains coupled to the central chain, wherein at least one side chain comprises a silicone moiety. In certain embodiments of the invention, the analyte modulating layer comprises a blended mixture of: a linear polyurethane/polyurea polymer, and a branched acrylate polymer; and the linear polyurethane/polyurea polymer and the branched acrylate polymer are blended at a ratio of between 1:1 and 1:20 (e.g. 1:2) by weight %. Typically, this analyte modulating layer composition comprises a first polymer formed from a mixture comprising a diisocyanate; at least one hydrophilic diol or hydrophilic diamine; and a siloxane; that is blended with a second polymer formed from a mixture comprising: a 2-(dimethylamino)ethyl methacrylate; a methyl methacrylate; a polydimethyl siloxane monomethacryloxypropyl; a poly(ethylene oxide) methyl ether methacrylate; and a 2-hydroxyethyl methacrylate. As disclosed herein, additional material layers can be included in such apparatuses. For example, in some embodiments of the invention, the apparatus comprises a high-density amine layer which is disposed between and in direct contact with the analyte sensing layer and the analyte modulating layer so as to exhibit a number of beneficial properties including an ability to provide a smoother surface structure and further promote adhesion between the analyte sensing layer and the analyte modulating layer. Without being bound by a specific scientific theory or mechanism of action, it is believed that adhesion between layers is promoted by smoother layer contact architectures as well as Vander Waals force interactions between the HDA polymers in the HDA layer and compounds present in the analyte sensing layer that is disposed on a first side of this HDA layer, and Vander Waals force interactions between the HDA polymers and compounds present in the analyte modulating layer that is disposed on a second side of this HDA layer (i.e. so that the HDA layer is in a "sandwich" configuration).

Figure 2A:
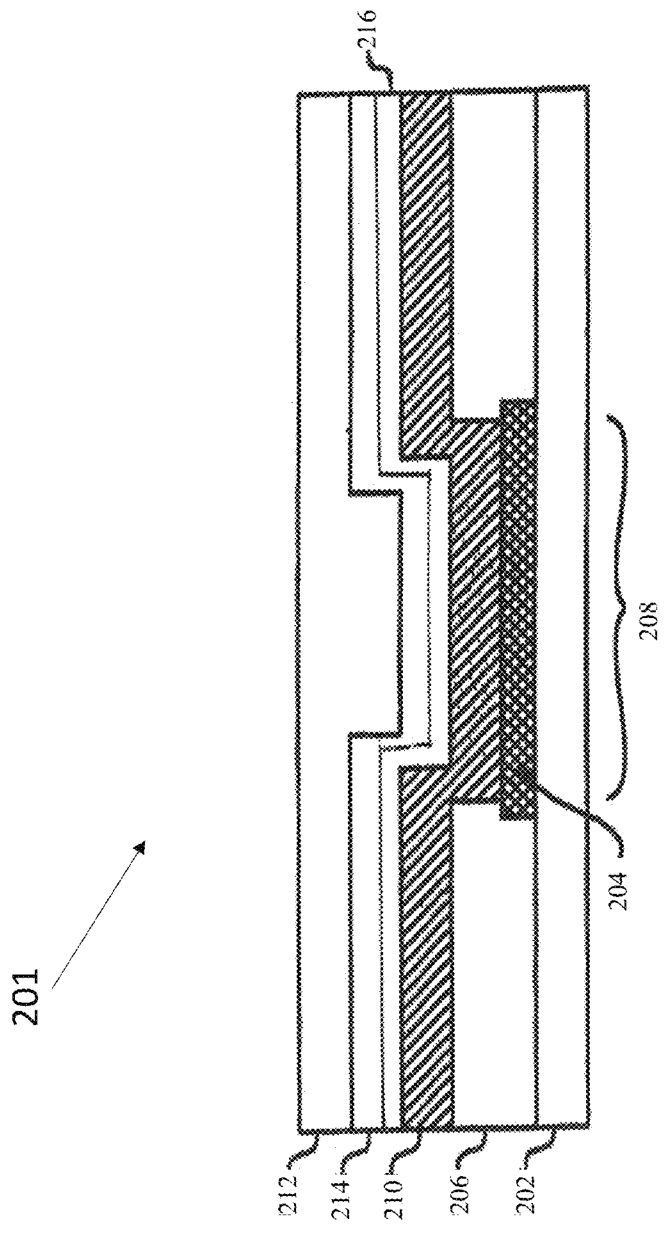
FIGS. 2A-2B provide schematics showing a conventional (PRIOR ART) sensor design comprising an amperometric analyte sensor formed from a plurality of planar layered elements which include albumin protein layer and an adhesion promoter layer (FIG. 2A); and a schematic showing differences between such conventional multilayer sensor stacks and sensor stacks having a high density amine layer (FIG. 2B).
Figure 2B:
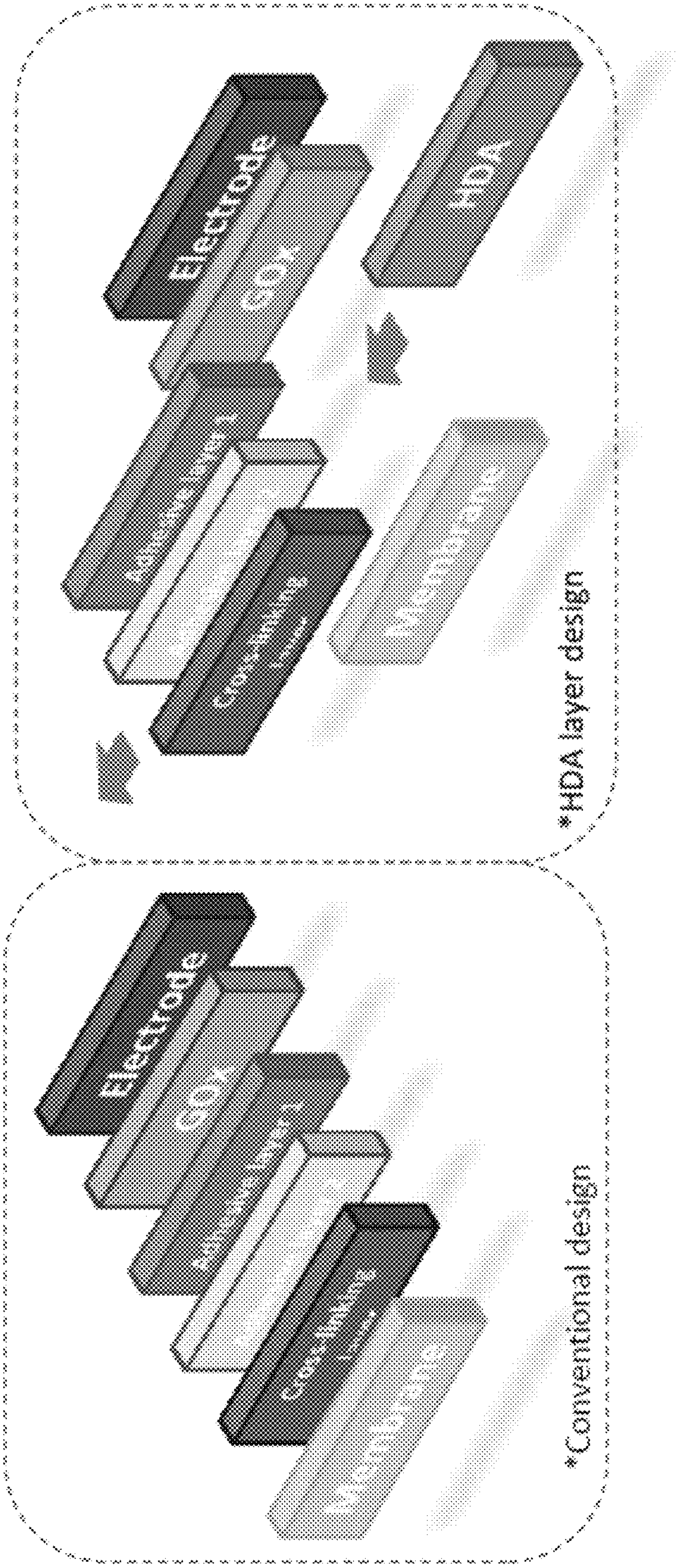

One prior art conventional sensor embodiment shown in FIG. 2A is a amperometric sensor 201 having a plurality of layered elements including a base layer 202, a conductive layer 204 (e.g. one comprising the plurality of electrically conductive members) which is disposed on and/or combined with the base layer 202. The following comments relate to this conventional sensor which is described to help understand the differences between such conventional sensors and the invention disclosed herein. Typically, the conductive layer 204 comprises one or more electrodes. An analyte sensing layer 210 (typically comprising an enzyme such as glucose oxidase) is disposed on one or more of the exposed electrodes of the conductive layer 204. A protein layer 216 disposed upon the analyte sensing layer 210. An analyte modulating layer 212 is disposed above the analyte sensing layer 210 to regulate analyte (e.g. glucose) access with the analyte sensing layer 210. An adhesion promoter layer 214 is disposed between layers such as the analyte modulating layer 212 and the analyte sensing layer 210 as shown in FIG. 2A in order to facilitate their contact and/or adhesion. This embodiment also comprises a cover layer 206 such as a polymer coating can be disposed on portions of the sensor 201. Apertures 208 can be formed in one or more layers of such sensors. Amperometric glucose sensors having this type of design are disclosed, for example, in U.S. Patent Application Publication Nos. 20070227907, 20100025238, 20110319734 and 20110152654, the contents of each of which are incorporated herein by reference. FIG. 2B shows a comparison between these conventional multilayer sensor stacks comprising a HDA layer.

Embodiments of the invention also provide articles of manufacture and kits for observing a concentration of an analyte. In an illustrative embodiment, the kit includes a sensor comprising a multilayer sensor stack as discussed herein. In typical embodiments, the sensors are disposed in the kit within a sealed sterile dry package. Optionally the kit comprises an insertion device that facilitates insertion of the sensor. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. The kit and/or sensor set may include other materials desirable from a commercial and user standpoint, including buffers, diluents, filters, needles, syringes, and package inserts with instructions for use.

Specific aspects of embodiments of the invention are discussed in detail in the following sections.

Typical Elements, Configurations and Analyte Sensor Embodiments of the Invention A. Typical Elements Found in of Embodiments of the Invention FIG. 2A illustrates a cross-section of a conventional sensor embodiment 201. The components of the sensor are typically characterized herein as layers in this layered electrochemical sensor stack because, for example, it allows for a facile characterization of conventional sensor structures such as those shown in FIG. 2A and their differences from the embodiment shown in FIG. 2B (i.e. ones comprising a HDA layer). Artisans will understand, that in certain embodiments of the invention, the sensor constituents are combined such that multiple constituents form one or more heterogeneous layers. In this context, those of skill in the art understand that, while certain layers/components of conventional sensor embodiments are useful in the HDA sensors disclosed herein, the placement and composition of the layered constituents is very different in HDA sensor embodiments of the invention. Those of skill in this art will understand that certain embodiments if the invention include elements/layers that are found in conventional sensors while others are excluded, and/or new material layers/elements are included. For example, certain elements disclosed in FIG. 2A are also found in the invention disclosed herein (e.g. a base, analyte sensing layer, an analyte modulating layer etc.) while, as shown in FIG. 2B, other elements are not (e.g. separate HSA protein layers, layers comprising a siloxane adhesion promoter etc.). Similarly, embodiments of the invention include layers/elements having materials disposed as shown in FIG. 2B or in other unique configurations that are not found in conventional sensors (e.g. high-density amine (HDA) polymer layers HDA).

The conventional embodiment shown in FIG. 2A includes a base layer 202 to support the sensor 201. The base layer 202 can be made of a material such as a metal and/or a ceramic and/or a polymeric substrate, which may be self-supporting or further supported by another material as is known in the art. Embodiments can include a conductive layer 204 which is disposed on and/or combined with the base layer 202. Typically, the conductive layer 204 comprises one or more electrically conductive elements that function as electrodes. An operating sensor 201 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 202 and/or conductive layer 204 can be generated using many known techniques and materials. In certain embodiments of the invention, the electrical circuit of the sensor is defined by etching the disposed conductive layer 204 into a desired pattern of conductive paths. A typical electrical circuit for the sensor 201 comprises two or more adjacent conductive paths with regions at a proximal end to form contact pads and regions at a distal end to form sensor electrodes. An electrically insulating cover layer 206 such as a polymer coating can be disposed on portions of the sensor 201. Acceptable polymer coatings for use as the insulating protective cover layer 206 can include, but are not limited to, non-toxic biocompatible polymers such as silicone compounds, polyimides, biocompatible solder masks, epoxy acrylate copolymers, or the like. In the sensors of the present invention, one or more exposed regions or apertures 208 can be made through the cover layer 206 to open the conductive layer 204 to the external environment and to, for example, allow an analyte such as glucose to permeate the layers of the sensor and be sensed by the sensing elements. Apertures 208 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 208. The exposed electrodes and/or contact pads can also undergo secondary processing (e.g. through the apertures 208), such as additional plating processing, to prepare the surfaces and/or strengthen the conductive regions.

In the conventional sensor configuration shown in FIG. 2A, an analyte sensing layer 210 is disposed on one or more of the exposed electrodes of the conductive layer 204. Typically, the analyte sensing layer 210 is an enzyme layer. Most typically, the analyte sensing layer 210 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 210 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic Diabetes.

In embodiments of the invention, the analyte sensing layer 210 can be applied over portions of the conductive layer or over the entire region of the conductive layer. Typically, the analyte sensing layer 210 is disposed on the working electrode which can be the anode or the cathode. Optionally, the analyte sensing layer 210 is also disposed on a counter and/or reference electrode. Methods for generating a thin analyte sensing layer 210 include brushing the layer onto a substrate (e.g. the reactive surface of a platinum black electrode), as well as spin coating processes, dip and dry processes, low shear spraying processes, ink-jet printing processes, silk screen processes and the like.

In this context, a variety of spin coating materials and methods are known in the art (see, e.g. Sahu et al., Indian J. Phys. 83 (4) 493-502 (2009), and U.S. Patent Publications 20020127878, 20020127878, 20090285982 and 20140272704). In certain embodiments of the invention, the material of the high-density amine layer comprising polymers having a plurality of repeating amine groups (e.g. poly-1-lysine polymers) is blended with another material such as a solvent or other agent that modulates solution viscosity in order to optimize spin coating uniformity. In this context, to prepare an HDA layer for spin coating, one can mix a viscosity modulating agent and/or one or two or more solvents together. For example, with two solvents one can use a major component of something that evaporates relatively quickly and a minor component of something that is relatively slow to evaporate. By using this combination, it is often possible to optimize aspects of this process in that during the spin coating process the major component evaporates quickly to give good coverage and a uniform thick film, and the remaining minor component still leaves enough plasticity for the molecules to organize before the film is completely dry.

The analyte modulating membrane layer 212 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In typical embodiments of the invention, a layer of materials comprising a high-density amine composition layer is disposed between the analyte modulating layer 212 and the analyte sensing layer 210 as shown in FIG. 2B in order to facilitate their contact and/or adhesion. In typical embodiments of the invention, the high-density amine layer comprises a first side in direct contact with the analyte sensing layer, and a second side in direct contact with the analyte modulating layer and functions as an adhesive layer that binds the analyte sensing layer to the analyte modulating layer. Optionally, the analyte sensing layer comprises glucose oxidase disposed in the layer so that the analyte sensor senses glucose; and the high-density amine layer HDA further functions to decrease sensor signal changes that result from fluctuating levels of oxygen ($O_2$). In certain embodiments of the invention, the poly-1-lysine in the high-density amine layer HDA has molecular weights between 30 KDa and 300 KDa, for example, molecular weights between 150 KDa and 300 KDa. Typically, the poly-1-lysine in the high-density amine layer HDA is in amounts from 0.1 weight-to-weight percent to 0.5 weight-to-weight percent. Optionally, the high-density amine layer HDA is from 0.1 to 0.4 microns thick.

B. Typical Analyte Sensor Constituents of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that selected elements from these thin film analyte sensors can be adapted for use in a number of sensor systems such as those described herein.

Base Constituent

Sensors of the invention typically include a base constituent (see, e.g. element 202 in FIG. 2A). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like. In some sensor embodiments, the electrode(s) on the base are organized/disposed within a flex-circuit assembly (i.e. a circuitry assembly that utilizes flexible rather than rigid materials).

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 204 in FIG. 2A). The term "conductive constituent" is used herein according to art accepted terminology. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 210 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure (and can for example be connected by vias through the sensor material(s) to the surfaces on which the electrodes are disposed). In certain embodiments of the invention, the reactive surfaces of the electrodes are of different relative areas/sizes, for example a 1× reference electrode, a 2.6× working electrode and a 3.6× counter electrode.

Analyte Sensing Constituent

The electrochemical sensors of the invention include an analyte sensing constituent disposed on the electrodes of the sensor (see, e.g. element 210 in FIG. 2A). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard, the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Some sensor embodiments of this element of the invention utilize an enzyme (e.g. glucose oxidase) that optionally has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide.

As noted above, the enzyme and the second protein (e.g. an albumin) can be treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture (however in certain embodiments of the invention disclosed herein, glutaraldehyde is excluded because the addition of a cross-linking reagent to the protein mixture creates a less active protein paste).

Alternative embodiments of analyte sensing constituents are not formed using glutaraldehyde, and are instead formed to include entrapped and/or crosslinked polypeptides such as glucose oxidase crosslinked to polyvinyl alcohol (PVA, see, e.g. CAS number 9002-89-5) polymers. As is known in the art, polyvinyl alcohol reacts with aldehydes to form water insoluble polyacetals. In a pure PVA medium having a pH around 5.0, polymer reaction with dialdehydes is expected to form an acetal cross-linked structure. In certain embodiments of the invention, such crosslinking reactions can be performed using a chemical vapor deposition (CVD) process. Due to the acidity of the PVA polymer solution, crosslinking reactions in CVD systems are simple and routine. Moreover, acidic conditions can be created by introducing compounds such as acetic acid into glutaraldehyde solutions, so a CVD system can provide an acid vapor condition. In addition the pH of the polymer medium can be adjusted by adding acidic compounds such as citric acid, polymer additives such as polylysine, HBr and the like.

Embodiments of the analyte sensing constituents include compositions having properties that make them particularly well suited for use in ambulatory glucose sensors of the type worn by diabetic individuals. Such embodiments of the invention include PVA-SbQ compositions for use in layered analyte sensor structures that comprise between 1 mol % and 12.5 mol % SbQ. In certain embodiments of the invention that are adapted or use in glucose sensors, the constituents in this layer are selected so that the molecular weight of the polyvinyl alcohol is between 30 kilodaltons and 150 kilodaltons and the SbQ in the polyvinyl alcohol is present in an amount between 1 mol % and 4 mol %. In some embodiments of the invention the analyte sensing layer is formed to comprise from 5% to 12% PVA by weight. In some embodiments of the invention the analyte sensing layer is formed to comprise glucose oxidase in an amount from 10 KU/mL to 20 KU/mL.

Embodiments of the analyte sensing constituents include analyte sensing layers selected for their ability to provide desirable characteristics for implantable sensors. In certain embodiments of the invention an amount or ratio of PVA within the composition is used to modulate the water adsorption of the composition, the crosslinking density of the composition etc. Such formulations can readily be evaluated for their effects on phenomena such as $H_2O$ adsorption, sensor isig drift and in vivo start up profiles. Sufficient $H_2O$ adsorption can help to maintain a normal chemical and electrochemical reaction within amperometric analyte sensors. Consequently, it is desirable to form such sensors from compositions having an appropriate hydrophilic chemistry. In this context, the PVA-GOx compositions disclosed herein can be used to create electrolyte hydrogels that are useful in internal coating/membrane layers and can also be coated on top of an analyte modulating layer (e.g. a glucose limiting membrane or "GLM") in order to improve the biocompatibility and hydrophilicity of the GLM layer.

As noted above, in some embodiments of the invention, the analyte sensing constituent includes an agent (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Protein Constituent

The electrochemical sensors of the invention optionally include a protein constituent disposed between the analyte sensing constituent and the analyte modulating constituent (see, e.g. element 216 in FIG. 2). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 214 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

High-density Amine Constituent

The electrochemical sensors of the invention can include one or more high-density amine constituent layers (see, e.g. HDA in FIG. 2B) that provide the sensors with a number of beneficial functions. Such layers can optimize sensor function, for example by acting as an adhesion promoting constituent for layers adjacent to the HDA layer, by decreasing fluctuations that can occur in glucose oxidase based sensors in the presence of fluctuating concentration of oxygen, by improving sensor initialization profiles and the like. The term "adhesion promoting constituent" is used herein according to art accepted terminology and refers to a constituent that includes materials selected for their ability to promote adhesion between adjoining constituents in the sensor. Typically, the high-density amine adhesion promoting constituent is disposed between and in direct contact with the analyte sensing constituent and the analyte modulating constituent. In typical embodiments, the high-density amine layer HDA comprises poly-1-lysine having molecular weights between 30 KDa and 300 KDa (e.g. between 150 KDa and 300 KDa). The concentrations of poly-1-lysine in such high-density amine layers HDA is typically from 0.1 weight-to-weight percent to 0.5 weight-to-weight percent and the high-density amine layer HDA is from 0.1 to 0.4 microns thick. In embodiments where the analyte sensing layer comprises glucose oxidase so that the analyte sensor senses glucose, and the high-density amine layer HDA functions to decrease sensor signal changes that result from fluctuating levels of oxygen ($O_2$).

Analyte Modulating Constituent

The electrochemical sensors of the invention include an analyte modulating constituent disposed on the sensor (see, e.g. element 212 in FIG. 2A). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The analyte modulating sensor membrane assembly serves several functions, including selectively allowing the passage of glucose therethrough (see, e.g. U.S. Patent Application No. 2011-0152654).

Cover Constituent

The electrochemical sensors of the invention can include one or more cover constituents which are typically electrically insulating protective constituents (see, e.g. element 206 in FIG. 2). Typically, such cover constituents can be in the form of a coating, sheath or tube and are disposed on at least a portion of the analyte modulating constituent. Typically such features comprise a polymer comprising a surface having the constellation of features disclosed herein that function to modulate immune response. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

C. Typical Analyte Sensor System Embodiments of the Invention

Embodiments of the sensor elements and sensors can be operatively coupled to a variety of other system elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Figure 4:
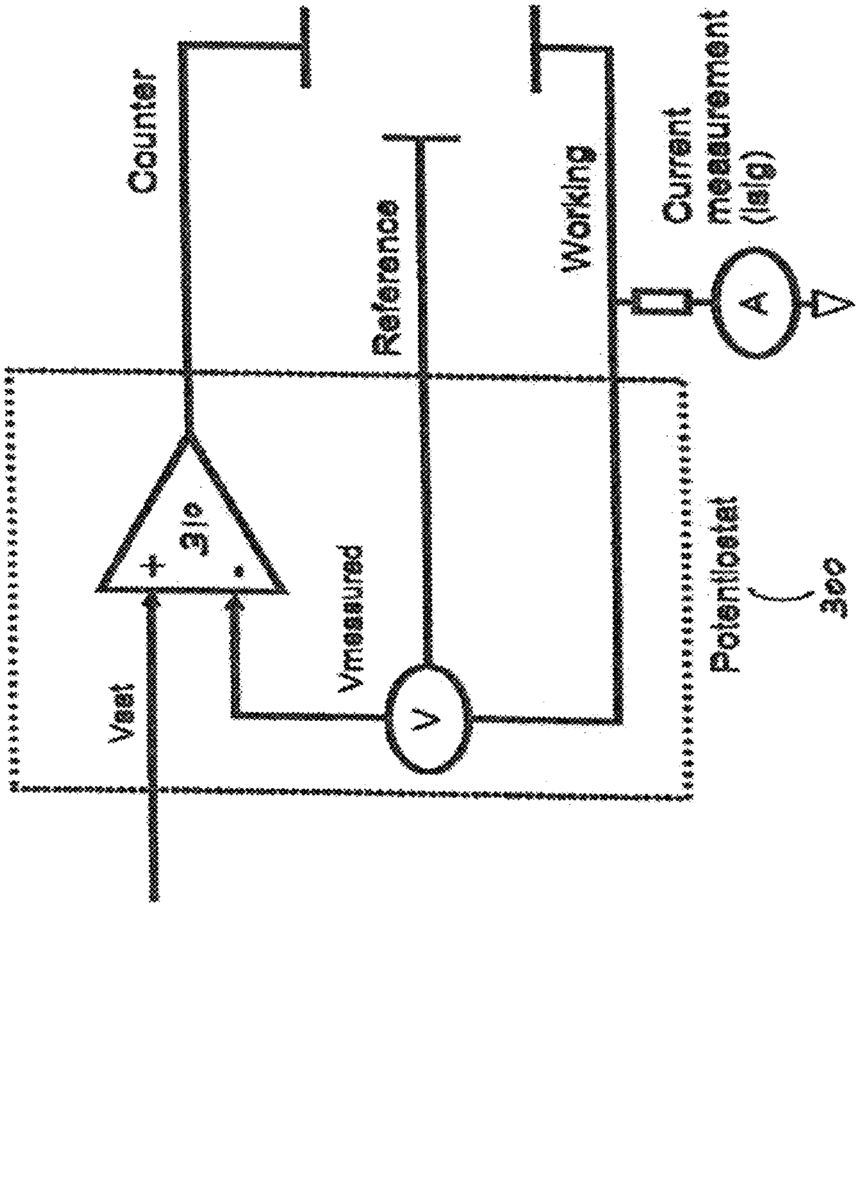
FIG. 4 shows a schematic of a potentiostat that may be used to measure current in embodiments of the present invention.

FIG. 4 shows a schematic of a potentiostat that may be used to measure current in embodiments of the present invention. As shown in FIG. 4, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

Embodiments of the invention include devices which process display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide providing real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically, in such devices, the physiological characteristic values include a plurality of measurements of blood glucose.

Figure 3:
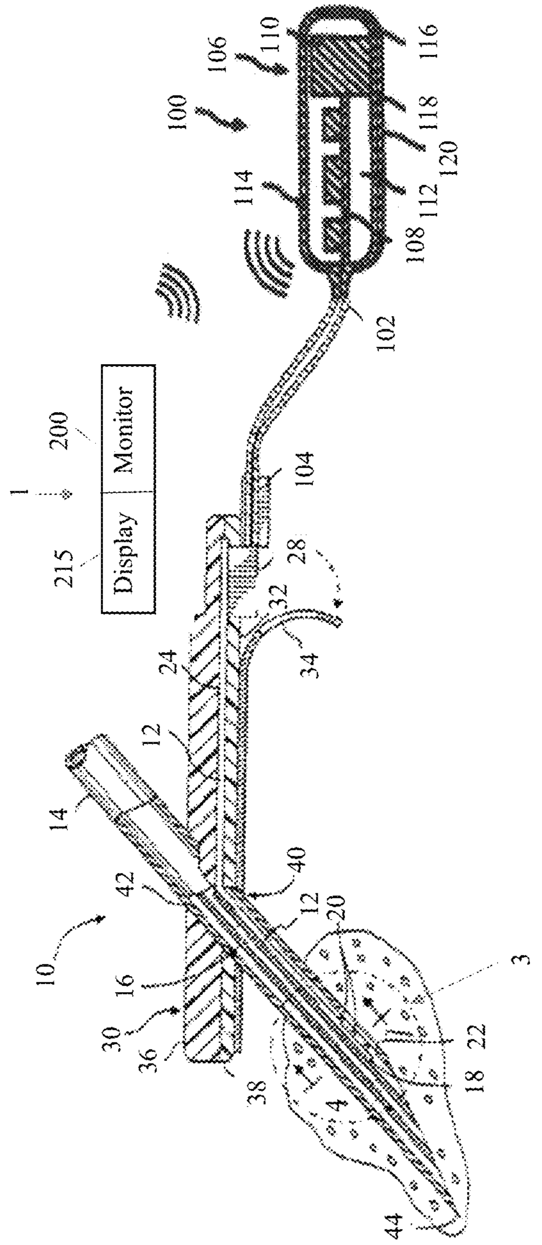
FIG. 3 provides a perspective view illustrating a subcutaneous sensor insertion set, a telemetered characteristic monitor transmitter device, and a data receiving device embodying features of the invention.

FIG. 3 provides a perspective view of one generalized embodiment of subcutaneous sensor insertion system and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 3 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 215 for monitoring a user's condition in response to signals derived from the sensor electrodes 20. The connection portion 24 may be conveniently connected electrically to the monitor 200 or a characteristic monitor transmitter 100 by a connector block 28 (or the like).

As shown in FIG. 3, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 100 is coupled to a sensor set 10 by a cable 102 through a connector 104 that is electrically coupled to the connector block 28 of the connector portion 24 of the sensor set 10.

In the embodiment shown in FIG. 3, the telemetered characteristic monitor 100 includes a housing 106 that supports a printed circuit board 108, batteries 110, antenna 112, and the cable 102 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 100 is ready for use.

In the illustrative embodiment shown in FIG. 3, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. Nos. 4,562,751; 4,678,408; 4,685,903 or 4,573,994, to control delivery of insulin to a diabetic patient.

In the illustrative embodiment shown in FIG. 3, the sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 3, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 102 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

EXAMPLES

Common acronyms used in the examples include: GOx Glucose Oxidase and GLM Glucose Limiting Membrane (an embodiment of an analyte modulating layer)

First Example: Simulation of $H_2O_2$

Figure 5B:
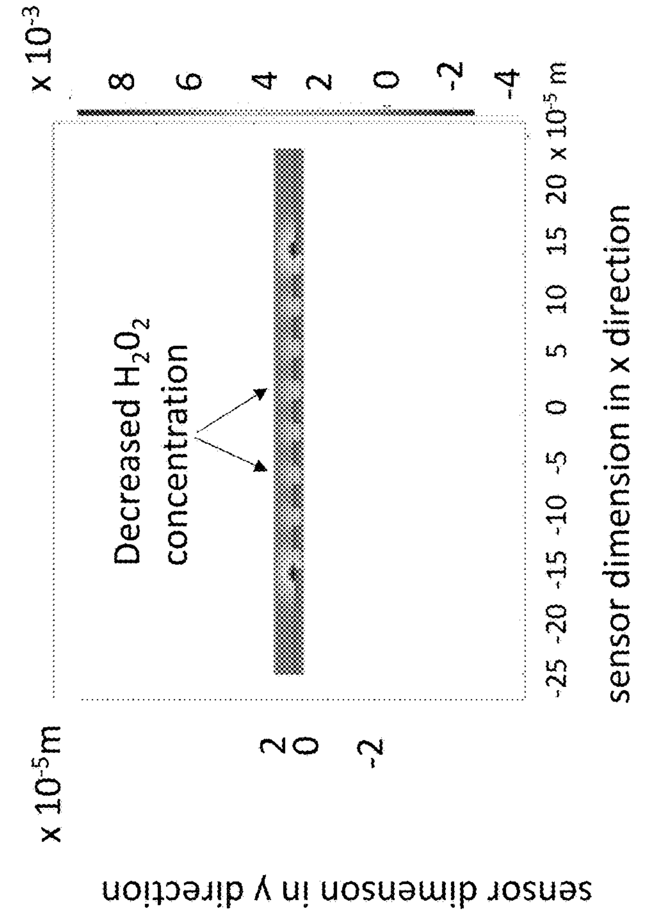
FIG. 5B. Simulation (using COMSOL software) of $H_2O_2$ concentration in the working electrode illustrated in FIG. 1A having an arrangement of micropillars according to one or more embodiments of the present invention, wherein the color contour plot and color bar are for surface $H_2O_2$ and as a function of position (y axis shows position in a y axis direction, x axis shows position in an x axis direction, units$\times 10^{-5}$ meters (m)), wherein darker/red shade indicates higher $H_2O_2$ concentration.
Figure 5A:
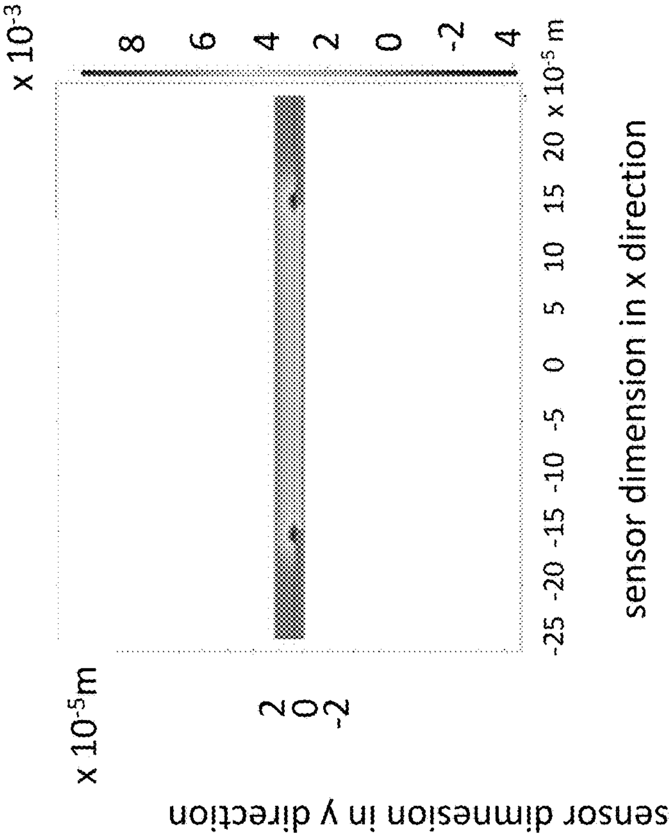
FIG. 5A. Simulation (using COMSOL software) of $H_2O_2$ concentration in the working electrode illustrated in FIG. 2A without an arrangement of pillars, wherein color contour plot and color bar are for surface $H_2O_2$ and darker/red shade indicates higher $H_2O_2$ concentration, as a function of position (y axis shows position in a y axis direction, x axis shows position in an x axis direction, units$\times 10^{-5}$ meters (m)).

FIG. 5A illustrates a COMSOL simulation of the $H_2O_2$ concentration in a nominal working electrode of a sensor as illustrated in FIG. 2A, wherein the working electrode includes a well but does not include an arrangement of pillars as described herein.

FIG. 5B illustrates a COMSOL simulation of the $H_2O_2$ concentration in a working electrode of a sensor, wherein the working electrode includes an arrangement of pillars as described herein (e.g., as illustrated in FIG. 1A). FIG. 5B illustrates that the working electrode having an arrangement of pillars reduces diffusion of the $H_2O_2$ molecules to the overlying analyte modulation layer (GLM) as compared to the nominal working electrode illustrated in FIG. 5A.

Third Example: Simulation of External $O_2$ Concentration

A typical electrochemical glucose sensor works according to the following chemical reactions:

$$\text{GLUCOSE} + O_2 \xrightarrow{\text{GLUCOSE OXIDASE}} \text{GLUCONIC ACID} + H_2O_2 \quad \text{Equation 1}$$

$$H_2O_2 \rightarrow O_2 + 2H^+ + 2e^- \quad \text{Equation 2}$$

The glucose oxidase is used to catalyze the reaction between glucose and oxygen to yield gluconic acid and hydrogen peroxide as shown in equation 1. The $H_2O_2$ reacts electrochemically as shown in equation 2, and the current is measured by a potentiostat. The stoichiometry of the reaction provides challenges to developing in vivo sensors. In particular, for optimal glucose oxidase based sensor performance, sensor signal output should be determined only by the analyte of interest (glucose), and not by any co-substrates ($O_2$) or kinetically controlled parameters such as diffusion. If oxygen and glucose are present in equimolar concentrations, then the $H_2O_2$ is stoichiometrically related to the amount of glucose that reacts with the glucose oxidase enzyme; and the associated current that generates the sensor signal is proportional to the amount of glucose that reacts with the enzyme. If, however, there is insufficient oxygen for all of the glucose to react with the enzyme, then the current will be proportional to the oxygen concentration, not the glucose concentration. Consequently, for a glucose sensor to provide a signal that depends solely on the concentrations of glucose, glucose must be the limiting reagent, i.e. the $O_2$ concentration must be in excess for all potential glucose concentrations. A problem with using such glucose sensors in vivo, however, is that the oxygen concentration where the sensor is implanted in vivo is low relative to glucose, a phenomenon which can compromise the accuracy of glucose sensor readings (and consequently, this phenomenon is termed the "oxygen deficit problem").

In view of issues such as the oxygen deficit problem discussed above, there is a need in the art for electrochemical sensors having architectures and materials selected to avoid the oxygen deficit problem and facilitate sensor function. Embodiments of the invention disclosed herein meet these as well as other needs.

Figure 6B:
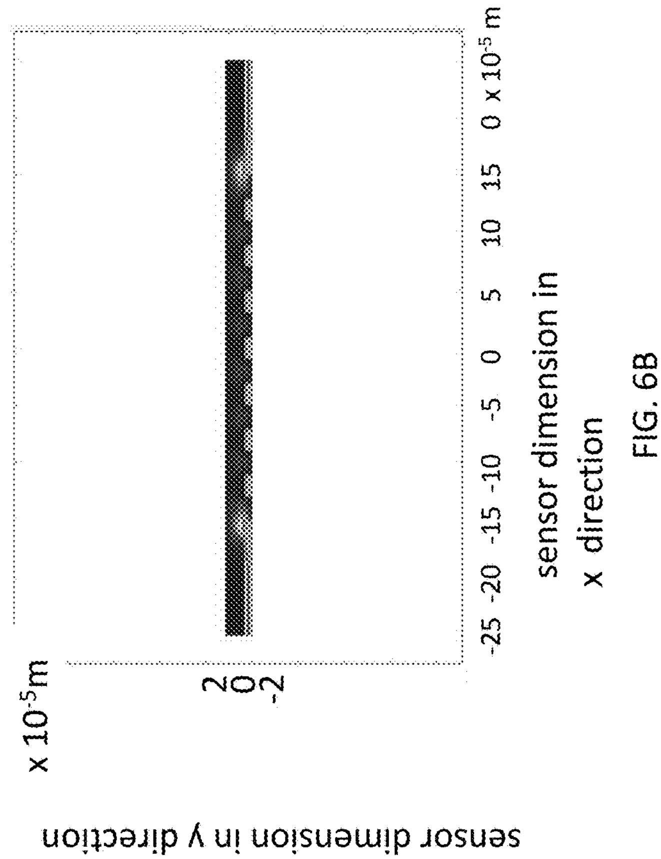
FIG. 6B. Simulation (using COMSOL software) of oxygen concentration in the working electrode illustrated in FIG. 1A with an arrangement of micropillars according to one or more embodiments of the present invention, wherein the color contour plot and color bar is for surface $O_2$ concentration as a function of position (y axis shows position in a y axis direction, x axis shows position in an x axis direction, units$\times 10^{-5}$ meters (m)).
Figure 6A:
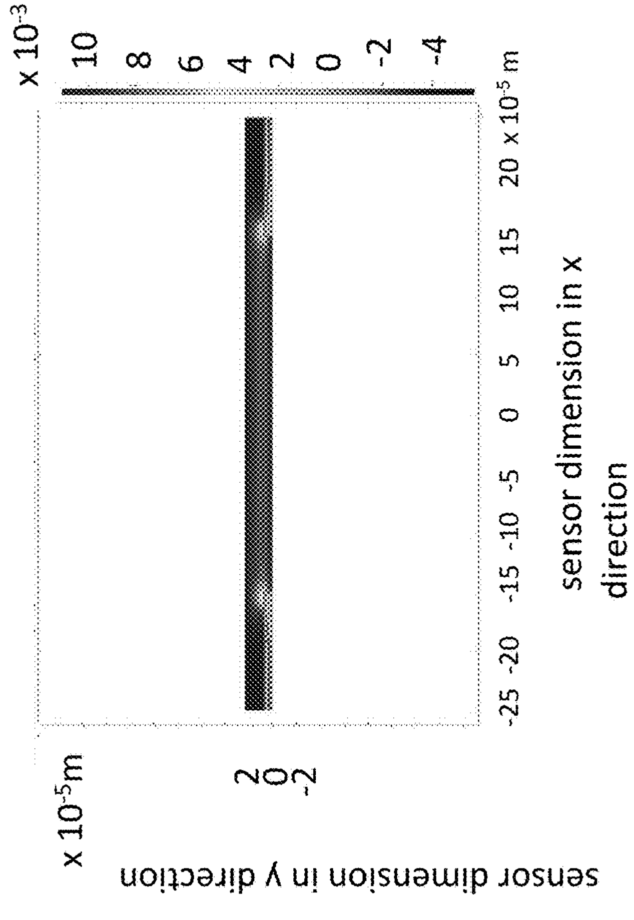
FIG. 6A. Simulation (using COMSOL software) of oxygen concentration in the working electrode illustrated in FIG. 2A without an arrangement of pillars, wherein the color contour plot and color bar is for surface $O_2$ concentration as a function of position (y axis shows position in a y axis direction, x axis shows position in an x axis direction, units$\times 10^{-5}$ meters (m)).

FIG. 6A illustrates a COMSOL simulation of the oxygen concentration in a nominal working electrode of a glucose sensor as illustrated in FIG. 2A, wherein the working electrode includes a well but does not include an arrangement of pillars as described herein. FIG. 6B illustrates the current density generated by the working electrode illustrated in FIG. 6A as a function of external oxygen concentration (mol/$m^3$).

Figure 6C:
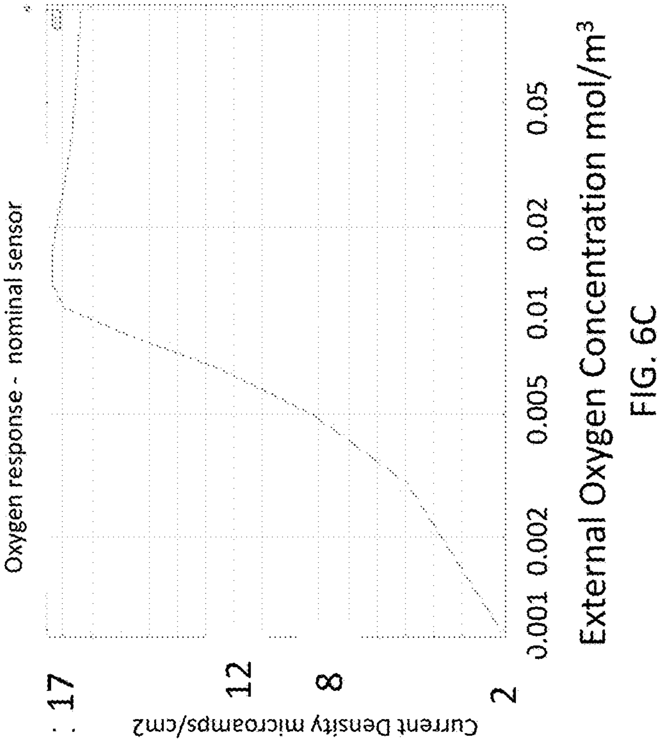
FIG. 6C. Current density (microamps per centimeter square) generated in the working electrode illustrated in FIG. 2A and FIG. 6A without an arrangement of micropillars, as a function of external oxygen concentration in a body being sensed using an electrochemical glucose sensor including the working electrode.
Figure 6D:
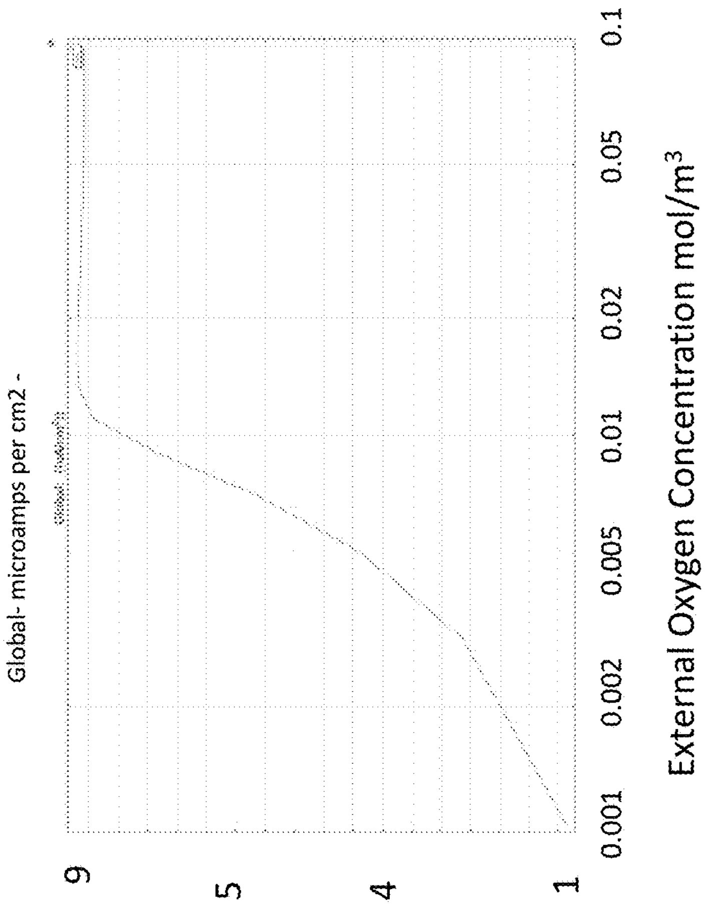
FIG. 6D. Current density (microamps per centimeter square) generated in the working electrode illustrated in FIG. 1A and FIG. 6B having micropillars according to one or more embodiments of the present invention, as a function of external oxygen concentration in a body being sensed using an electrochemical glucose sensor including the working electrode.
Figure 7:
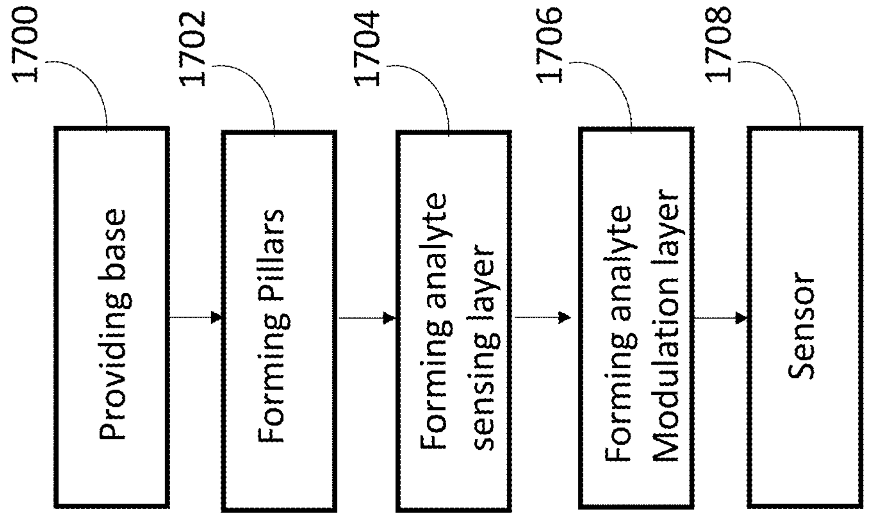
FIG. 7. Flowchart illustrating a method of making a sensor according to one or more embodiments.

FIG. 6C illustrates a COMSOL simulation of the oxygen concentration in a working electrode of a glucose sensor, wherein the working electrode includes an arrangement of pillars as described herein (see also FIG. 1A). FIG. 6D illustrates the current density generated by the working electrode illustrated in FIG. 6C as a function of external oxygen concentration (mol/$m^3$). FIG. 6E illustrates the current density generated by the working electrode illustrated in FIG. 6C as a function of external oxygen concentration (mol/$m^3$), for a different arrangement of pillars according to one or more embodiments of the present invention. Thus, FIGS. 6D and 6E illustrates the analyte modulation layer facilitates the diffusion of the oxygen from an external environment to the analyte sensing layer, and the arrangement of pillars distributes the oxygen throughout the channels so as to increase stability of the electrical current as a function of oxygen concentration, as compared to the nominal working electrode without the arrangement of pillars.

In one or more embodiments, the arrangement of pillars distributes the oxygen throughout the channels so as to increase stability of the electrical current as a function of oxygen concentration. In one or more examples, the increased stability is characterized as a reduced decay of the electrical current as the concentration of the oxygen is increased, as compared to the sensor without the pillars.

Example Embodiments

The present disclosure describes sensor and method embodiments including, but not limited to, the following.

1. An electrochemical analyte sensor 150 comprising a base layer 202*a*; a working electrode including an arrangement 152 of pillars 154 defining one or more channels 156 between the pillars 154; and a multilayer analyte sensor stack operably coupled to the arrangement 152 of pillars 154. The multilayer analyte sensor stack includes (a) an analyte sensing layer 210*a* including an enzyme having a composition that reacts with an analyte to form a byproduct, the byproduct detectably altering an electrical current Isig at the working electrode WE; and (b) an analyte modulating layer disposed over the analyte sensing layer 210*a*, wherein the analyte modulating layer 212*a* facilitates the diffusion of the analyte from an external environment (e.g., human body) to the analyte sensing layer 210*a*. The one or more channels 156 increase confinement of the byproduct in the channels 156 so as to increase interaction of the byproduct with the working electrode WE.
2. The sensor 150 of embodiment 1, wherein the channels 156 increase a number of diffusion directions 172 for the byproduct such that diffusion of the byproduct to the analyte modulation layer is reduced and diffusion 174 of the byproduct to sidewalls of the pillars 154 is increased.
3. The electrochemical analyte sensor 150 of embodiment 1 or 2, wherein the analyte comprises glucose, the enzyme comprises glucose oxidase, and the byproduct comprises hydrogen peroxide.
4. The electrochemical analyte sensor 150 of embodiments 1, 2, or 3, wherein:
   the analyte modulation layer 212*a* facilitates diffusion of the oxygen from an external environment to the analyte sensing layer 210*a*, and
   the arrangement 152 of the pillars 154 distributes the oxygen throughout the working electrode WE.
5. The electrochemical analyte sensor 150 of embodiments 1-4, wherein the pillars 154 have a diameter Din a range of 0.001-1000 micrometers, a height H in a range of 0.001-1000 micrometers, and a spacing S in a range of 0.001-1000 micrometers.
6. The electrochemical analyte sensor 150 of embodiments 1-4, wherein the pillars 154 have a diameter D in a range of 10-15 micrometers, a height H in a range of 10-15 micrometers, and a spacing S in a range of 10-15 micrometers.
7. The electrochemical analyte sensor 150 of embodiments 1-4, wherein the pillars 154 have a diameter D in a range of 5-25 micrometers, a height H in a range of 5-25 micrometers, and a spacing S in a range of 5-25 micrometers.
8. The electrochemical analyte sensor 150 of embodiments 1-4, wherein the pillars 154 have a diameter D in a range of 0.001-0.01 micrometers, a height H in a range of 0.001-0.01 micrometers, and a spacing S in a range of 0.001-0.01 micrometers.
9. The electrochemical analyte sensor 150 of embodiments 1-4, wherein the pillars 154 have a diameter D in a range of 0.001-0.01 micrometers, a height H in a range of 0.001-0.01 micrometers, and a spacing S in a range of 0.001-0.01 micrometers.
10. The electrochemical analyte sensor 150 of embodiments 1-4, wherein the pillars 154 have a diameter Din a range of 0.01-1 micrometers, a height H in a range of 0.01-1 micrometers, and a spacing S in a range of 0.01-1 micrometers.
11. The electrochemical analyte sensor 150 of embodiments 1-4, wherein the pillars 154 have a diameter D in a range of 1-10 micrometers, a height H in a range of 1-10 micrometers, and a spacing S in a range of 1-10 micrometers.
12. The electrochemical analyte sensor 150 of embodiments 1-4, wherein the pillars 154 are arranged in a hexagonal pattern 164.
13. The electrochemical analyte sensor 150 of embodiments 1-12, wherein the pillars 154 are arranged in a serpentine pattern 128.

14. The electrochemical analyte sensor 150 of embodiments 1-12, wherein the analyte sensing layer 210*a* is at least partially disposed in the channels 156 in spaces 162 between the pillars 154.
15. The electrochemical analyte sensor 150 of embodiments 1-12, wherein the analyte modulation layer is disposed directly on top T of the pillars 154.
16. The sensor 150 of claim embodiments 1-12, wherein the pillars 154 include a metal composition 160 comprising at least one metal selected from platinum, gold, silver, copper, titanium, chromium, and iridium.
17. A sensor electrode 150*a*, comprising a base substrate (e.g., 202*a*); an electrode (e.g., WE) including an arrangement 152 of pillars 154 disposed on the base substrate, wherein the pillars 154 form an electroactive surface of the electrode, and an analyte sensing layer 210*a* coupled to the electrode, the analyte sensing layer 210*a* having a composition that reacts with an analyte to form a byproduct, the byproduct detectably altering an electrical current Isig at the electrode. The arrangement 152 of the pillars 154 defines one or more channels 156 between the pillars 154, the one or more channels 156 increasing confinement of the byproduct in the channels 156 so as to increase interaction of the byproduct with the electroactive surface during sensing of the analyte.

FIG. 17 is a flowchart illustrating a method of making a sensor, e.g., according to any of the embodiments 1-17.

Block 1700 represents providing a base layer 202*a*.

Block 1702 represents forming an arrangement 152 of pillars 154 defining one or more channels 156 over the base layer, wherein the arrangement of pillars includes a conductive layer 154*a* including a working electrode (e.g. WE). In one or more examples, forming the pillars comprises patterning base layer pillars 154*b* in the base layer 202*a* and depositing the conductive layer 154*a* on the base layer pillars so as to form the pillars 154.

Block 1704 represents forming an analyte sensing layer 210*a* operably coupled to the arrangement of the pillars, the analyte sensing layer including an enzyme having a composition that reacts with an analyte to form a byproduct, the byproduct detectably altering an electrical current at the working electrode.

Block 1706 represents forming an analyte modulating layer 212*a* over the analyte sensing layer, wherein the analyte modulating layer facilitates the diffusion of the analyte from an external environment to the analyte sensing layer.

The layers 202*a*, 210*a*, 212*a* and the pillars 154 are disposed so that the one or more channels 156 increase confinement of the byproduct in the one or more channels such that interaction of the byproduct with the working electrode is increased; and so that the electrochemical analyte sensor 150 is made, as represented by Block 1708 (e.g., as illustrated in FIGS. 1A-1D or according to embodiments 1-17 above).

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The invention claimed is:

1. A glucose sensor comprising a sensor electrode, comprising:
the sensor electrode comprising:
a base substrate;
a working electrode including an arrangement of pillars defining channels disposed on the base substrate, wherein the pillars form an electroactive surface of the working electrode; and
an analyte sensing layer coupled to the working electrode, the analyte sensing layer comprising glucose oxidase catalyzing a reaction between glucose and oxygen, from an external environment, to form a byproduct comprising hydrogen peroxide, the byproduct detectably altering an electrical current at the working electrode; and
an analyte modulating layer comprising a polymer disposed over and in contact with the analyte sensing layer; and
wherein the channels distribute the oxygen, after diffusion through a thickness of the analyte modulating layer to the analyte sensing layer, throughout the working electrode; and
a processor coupled to the sensor electrode, the processor configured for determining a concentration of the glucose from the electrical current by taking into account distribution of the oxygen by the channels, so as to obtain a more accurate reading of the concentration of the glucose as compared to a reading of the concentration using the working electrode without the arrangement of pillars.

2. The glucose sensor of claim 1, wherein the pillars have a diameter in a range of 0.001-1000 micrometers, a height in a range of 0.001-1000 micrometers, and a spacing in a range of 0.001-1000 micrometers.

3. The glucose sensor of claim 1, wherein the pillars have a diameter in a range of 10-15 micrometers, a height in a range of 10-15 micrometers, and a spacing in a range of 10-15 micrometers.

4. The glucose sensor of claim 1, wherein the pillars have a diameter in a range of 5-25 micrometers, a height in a range of 5-25 micrometers, and a spacing in a range of 5-25 micrometers.

5. The glucose sensor of claim 1, wherein the arrangement comprises a hexagonal pattern.

6. The glucose sensor of claim 1, wherein the arrangement comprises a serpentine pattern.

7. The glucose sensor of claim 1, wherein the analyte modulating layer is disposed directly on top of the pillars and over the analyte sensing layer across a width of the channels.

8. The glucose sensor of claim 1, wherein the glucose oxidase is at least partially disposed in the channels in spaces between the pillars.

9. The glucose sensor of claim 1, wherein the channels increase diffusion of the hydrogen peroxide towards sidewalls of the pillars.

10. The glucose sensor of claim 1, wherein the pillars include a metal composition comprising at least one metal selected from platinum, gold, silver, copper, titanium, chromium, or iridium.

11. The glucose sensor comprising the sensor electrode of claim 1, wherein the processor determines the concentration of glucose by associating the electrical current as being proportional to the concentration glucose.

12. The glucose sensor of claim 11, wherein the arrangement of pillars is such that the electrical current has increased stability, as characterized by a reduced decay of the electrical current as:

a concentration of the oxygen is increased, and as compared to the glucose sensor without the pillars.

13. The glucose sensor of claim 1, wherein the analyte modulating layer comprises a glucose limiting membrane contacting the working electrode and the analyte sensing layer across a spacing between the pillars.

14. The glucose sensor of claim 1, wherein the polymer comprises:

a hydrophilic comb-copolymer having a central chain and a plurality of side chains coupled to the central chain, wherein at least one side chain comprises a silicone moiety, a blended mixture of a linear polyurethane/polyurea polymer, and a branched acrylate polymer, a first polymer formed from a mixture comprising a diisocyanate; at least one hydrophilic diol or hydrophilic diamine; and a siloxane; that is blended with a second polymer formed from a mixture comprising a 2-(dimethylamino)ethyl methacrylate; a methyl methacrylate; a polydimethyl siloxane monomethacryloxypropyl; a poly(ethylene oxide) methyl ether methacrylate; and a 2-hydroxyethyl methacrylate, or a high-density amine layer.

15. A glucose sensor comprising a sensor electrode, comprising:

the sensor electrode comprising:

a base substrate;

an electrode including an arrangement of pillars defining channels disposed on the base substrate, wherein the pillars form an electroactive surface of the electrode; and an analyte sensing layer disposed in spaces between the pillars, wherein the analyte sensing layer comprises glucose oxidase for catalyzing a reaction between glucose and oxygen to form hydrogen peroxide altering an electrical current at the electrode;

an analyte modulating layer comprising a polymer contacting the electrode and the analyte sensing layer across the spaces between the pillars; and wherein the channels increase diffusion of the hydrogen peroxide to sidewalls of the pillars; and a processor coupled to the sensor electrode for determining a concentration of the glucose as being proportional to the electrical current by taking into account the diffusion of the hydrogen peroxide resulting from the arrangement of pillars.

16. The glucose sensor of claim 15, wherein the polymer comprises:

a hydrophilic comb-copolymer having a central chain and a plurality of side chains coupled to the central chain, wherein at least one side chain comprises a silicone moiety, a blended mixture of a linear polyurethane/polyurea polymer, and a branched acrylate polymer, a first polymer formed from a mixture comprising a diisocyanate; at least one hydrophilic diol or hydrophilic diamine; and a siloxane; that is blended with a second polymer formed from a mixture comprising a 2-(dimethylamino)ethyl methacrylate; a methyl methacrylate; a polydimethyl siloxane monomethacryloxypropyl; a poly(ethylene oxide) methyl ether methacrylate; and a 2-hydroxyethyl methacrylate, or a high-density amine layer.

17. A method of making a sensor electrode, comprising:

providing a base substrate;

forming a working electrode including an arrangement of pillars defining channels disposed on the base substrate, wherein the pillars form an electroactive surface of the working electrode; and coupling an analyte sensing layer to the working electrode, the analyte sensing layer comprising glucose oxidase catalyzing a reaction between glucose and oxygen to form a byproduct comprising hydrogen peroxide, the byproduct detectably altering an electrical current at the working electrode; and disposing an analyte modulating layer comprising a polymer in contact with the analyte sensing layer, for diffusion of the glucose and the oxygen through a thickness of the analyte modulating layer to the analyte sensing layer; and wherein the channels distribute the oxygen, after the diffusion through the thickness, throughout the working electrode; and coupling a processor to the sensor electrode and configuring the processor to determine a concentration of the glucose as being proportional to the electrical current by taking into account distribution of the oxygen by the channels, so as to obtain a more accurate reading of the concentration of the glucose as compared to a reading of the concentration using the working electrode without the arrangement of pillars.

18. The method of claim 17, wherein the analyte modulating layer is disposed directly on top of the pillars and over the analyte sensing layer in the channels.

19. The method of claim 17, wherein the glucose oxidase is at least partially disposed in the channels in spaces between the pillars.

20. The method of claim 17, wherein the channels are configured to increase diffusion of the hydrogen peroxide towards sidewalls of the pillars.

21. The method of claim 17, further comprising providing the sensor electrode in a glucose sensor.

* * * * *